(12) United States Patent
Schobben et al.

(10) Patent No.: US 12,370,362 B2
(45) Date of Patent: Jul. 29, 2025

(54) TISSUE STIMULATION DEVICE WITH DISTAL AND PROXIMAL RETURN ELECTRODE

(71) Applicant: SALVIA BIOELECTRONICS B.V., Eindhoven (NL)

(72) Inventors: Daniël Schobben, Eindhoven (NL); Hubert Martens, Eindhoven (NL)

(73) Assignee: Salvia BioElectronics B.V., Eindhoven (NL)

( * ) Notice: Subject to any disclaimer, the term of this patent is extended or adjusted under 35 U.S.C. 154(b) by 609 days.

(21) Appl. No.: 17/609,756

(22) PCT Filed: May 9, 2020

(86) PCT No.: PCT/IB2020/054407
§ 371 (c)(1),
(2) Date: Nov. 8, 2021

(87) PCT Pub. No.: WO2020/225798
PCT Pub. Date: Nov. 12, 2020

(65) Prior Publication Data
US 2022/0218986 A1    Jul. 14, 2022

(30) Foreign Application Priority Data
May 9, 2019 (NL) ..................................... 2023094

(51) Int. Cl.
*A61N 1/05* (2006.01)
(52) U.S. Cl.
CPC .................. *A61N 1/0551* (2013.01)
(58) Field of Classification Search
CPC .............. A61N 1/0551; A61N 1/0534; A61N 1/36007; A61N 1/36075; A61N 1/36182; A61N 1/36185; A61N 1/0531
See application file for complete search history.

(56) References Cited

U.S. PATENT DOCUMENTS

| | | | |
|---|---|---|---|
| 8,554,340 B2 * | 10/2013 | Janik | A61N 1/05 607/116 |
| 2008/0015669 A1 | 1/2008 | Jolly | |

(Continued)

OTHER PUBLICATIONS

Search Report for International Patent Application PCT/IB2020/054407, mailed on Nov. 12, 2020.

(Continued)

*Primary Examiner* — Mark W. Bockelman
(74) *Attorney, Agent, or Firm* — Fresh IP PLC; Clifford D. Hyra; Aubrey Y. Chen

(57) ABSTRACT

Typically, stimulation therapy is provided using one or more implanted stimulation electrodes. Anatomy and treatment protocols can vary greatly—it is therefore advantageous to provide a highly configurable stimulation system.

A tissue stimulation system is provided including an implantable end and a stimulation energy source, the implantable end including: an elongated substrate; one or more stimulation electrodes; and one or more proximal return electrodes; the stimulation energy source including: one or more distal return electrodes, disposed distantly from the one or more stimulation electrodes; and a pulse energy controller including a ratio controller, wherein: the proximal return electrodes and the distal return electrodes are configured as an electrical return for the stimulation electrodes; the ratio controller modifying the electrical potential and/or current ratio of the first part to the second part.

A substantially transverse electric field may be provided. In addition, a ratio controller may also be provided.

24 Claims, 9 Drawing Sheets

(56) References Cited

U.S. PATENT DOCUMENTS

| | | |
|---|---|---|
| 2010/0057165 A1 | 3/2010 | Moffitt |
| 2013/0116751 A1 | 5/2013 | Moffitt |
| 2015/0099959 A1 | 4/2015 | Bonmassar |
| 2021/0170175 A1* | 6/2021 | Schobben ............ A61N 1/0526 |

OTHER PUBLICATIONS

Christina Hassler et al: "Polymers for neural implants", Journal of Polymer Science Part B: Polymer Physics, vol. 49, No. 1, Nov. 23, 2010, pp. 18-33.

* cited by examiner

TISSUE STIMULATION DEVICE WITH DISTAL AND PROXIMAL RETURN ELECTRODE

FIELD

The present disclosure relates to a tissue stimulation system for providing electrical stimulation.

BACKGROUND

Implantable electrical stimulation systems may be used to deliver electrical stimulation therapy to patients to treat a variety of symptoms or conditions such as headaches, lower back pain and incontinence.

In many electrical stimulation applications, it is desirable for a stimulation system, typically comprising a therapeutic lead (a lead comprises electrodes and electrical connections), to provide electrical stimulation to one or more precise locations within a body. Typically, stimulation is provided using one or more stimulation electrodes that are configured to transfer electrical pulses to tissue with respect to one or more electrical returns.

US application US 2010/0057165 describes a neurostimulation paddle lead carrying a plurality of electrodes comprising at least four columns of electrodes having a spacing between two inner electrode columns less than a spacing between the inner electrode columns and adjacent outer electrode columns. The inner electrode columns may also be longitudinally offset from the outer electrode columns. The methods and neurostimulation systems steer current between the electrodes to modify a medial-lateral electrical field created adjacent spinal cord tissue.

US application US 2015/0099959 describes an implantable electrode array, including an organic substrate material configured to be implanted into an in vivo environment and to optionally dissolve after implantation and be absorbed, and an electrode mounted to the organic substrate material and configured to acquire signals generated by the in vivo environment. The electrode array includes a connection pad mounted to the organic substrate, and an MRI-compatible conductive trace formed between the electrode and the connection pad.

Anatomy and treatment protocols can vary greatly—it is therefore advantageous to provide a stimulation system that can be configured to a high degree. Systems and devices are known which comprise a plurality of electrodes proximate to each other in the lead, allowing one or more electrodes to be selected for use. Some electrodes may be selectable as either stimulation or return electrodes, allowing some tuning of the region of stimulation. The degree of electrical energy, such as voltage, current and/or power may also be varied, to provide some degree of control over the level of stimulation.

It is an object of the invention to provide an improved tissue stimulation system that provides additional configuration possibilities and adjustments.

GENERAL STATEMENTS

According to a first aspect of the present disclosure, there is provided a tissue stimulation system comprising an implantable end and a stimulation energy source, the implantable end comprising: an elongated substrate, disposed along a longitudinal axis, the substrate having a first and second surface disposed along substantially parallel transverse planes; one or more stimulation electrodes, comprised in the second surface and configured to transmit energy, in use, to human or animal tissue; and one or more proximal return electrodes, comprised in the first surface or second surface, disposed proximate the one or more stimulation electrodes; the stimulation energy source further comprising: one or more distal return electrodes, disposed distantly from the one or more stimulation electrodes; and a pulse energy controller; the tissue stimulation system further comprising: one or more interconnections between the implantable end and a stimulation energy source, configured and arranged to connect the output of the pulse generator to the one or more stimulation electrodes whereby electrical energy may be transferred, during use, as one or more electrical stimulation pulses to the one or more stimulation electrodes with respect to an electrical return; wherein: the one or more proximal return electrodes are configured as a first part of the electrical return for the one or more stimulation electrodes; and the one or more distal return electrodes are configured as a second part of the electrical return for the one or more stimulation electrodes; the pulse energy controller further comprising a ratio controller, configured and arranged to modify the electrical potential and/or current ratio of the first part to the second part.

By providing an implantable end with one or more proximal return electrodes proximate the one or more stimulation electrodes, a substantially transverse electric field may be provided. It may then provide a more concentrated current density and distribution in directions approximately perpendicular to the longitudinal axis (transversely-oriented electric field). This provides an additional degree of configuration for tissue stimulation systems and devices.

In addition, a potential and/or current ratio controller provides a convenient way to concentrate or diffuse this substantially transverse field in combination with one or more distal return electrodes comprised in the stimulation energy source: when the electrical return is mainly provided by the one or more proximal return electrodes in the implantable end, the electric field is stronger (more local). Alternatively, when the electrical return is mainly provided by the one or more distal return electrodes in the stimulation energy source, the electric field is weaker (more global).

It may be advantageous to configure and arrange the one or more distal return electrodes to be disposed more than 18 mm, preferably more than 24 mm, from the one or more corresponding stimulation electrodes. Additionally or alternatively, it may be advantageous to configure and arrange the one or more proximal return electrodes (400) to be disposed within less than 8 mm, preferably less than 6 mm, from the one or more corresponding stimulation electrodes.

In this context, corresponding means the one or more stimulation electrodes that are configured, in use, to transmit energy to tissue with respect to at least one distal and at least one proximal return electrode.

According to a further aspect of the present disclosure, there is provided a tissue stimulation system wherein the one or more proximal return electrodes are elongated along the longitudinal axis.

Having elongated electrodes provides stimulation over extended longitudinal dispositions.

According to another aspect of the present disclosure, there is provided a tissue stimulation system wherein the one or more stimulation electrodes have a first extent along the longitudinal axis, and the one or more proximal return electrodes have a second extent along the longitudinal axis, the second extent being substantially the same or greater than the first extent.

The control over the electric field is preferably provided over at least substantially the same length (extent along the longitudinal axis) as the one or more stimulation electrodes. If the proximal return electrodes are substantially longer (greater extent), they may be operated as a proximal return electrode for more than one stimulation electrode—so if another stimulation electrode is selected, a further reconfiguration of the electrodes may be avoided. In other words, if a different active stimulation electrode is selected, this typically results in stimulation energy being applied at a different longitudinal disposition. A substantially longer proximal return electrode may provide an electrical return for the currently selected stimulation electrode and the previously selected stimulation electrode.

According to a further aspect of the present disclosure, there is provided a tissue stimulation system wherein the one or more stimulation electrodes are elongated along the longitudinal axis.

By being elongated, stimulation energy may be applied over a plurality of dispositions along the longitudinal axis. This greatly reduces the chance that, after implantation, the electrode is not proximate enough to a stimulation target. Particularly, when the target is a nerve.

According to yet another aspect of the present disclosure, there is provided a tissue stimulation system wherein the one or more proximal return electrode comprises two proximal return electrode regions, electrically connected to each other, the two proximal return electrode regions being disposed on opposing sides of the one or more stimulation electrode.

By providing suitably configured return electrodes with two regions, treatment current density and the position where the highest current densities occur may be predetermined and/or controlled. In some cases, a very high degree of control may not be possible due to, for example, the nature of the treatment, the system and/or device, the implant site and the individual patient—in such cases, the configuration of the return electrodes may exert a degree of influence on the current density and its distribution.

According to a further aspect of the present disclosure, there is provided a tissue stimulation system wherein the two proximal return electrode regions are two non-contiguous electrode regions, electrically connected to each other; and each return electrode region is separated at least partially along the first transverse axis from the one or more stimulation electrodes by an electrical insulator.

As surface area and relative disposition are among the factors that influence treatment current density and distribution, providing at least two non-contiguous regions may provide a high degree of control. In addition, the shape and proximity to the corresponding stimulation electrode may also provide a degree of control.

According to a further aspect of the present disclosure, there is provided a tissue stimulation system wherein the two proximal return electrode regions are comprised in a substantially contiguous proximal return electrode.

In general, it is advantageous to maximize the tissue contact-area of the one or more return electrodes as this increase the efficiency of energy transfer to the tissue through the one or more stimulation electrodes. In addition, when using a substrate, such as LCP (Liquid Crystal Polymer), which may be easily manipulated using semiconductor processes known to the skilled person, such as deposition, etching and lithography this means that a high degree of control may be exerted on the shape, dimensions (extent), disposition and electrical, physical & mechanical properties of the return electrode.

According to a still further aspect of the present disclosure, there is provided a tissue stimulation system wherein one or more of the two proximal return electrode regions extend along the first transverse axis (700) between an edge of the one or more corresponding stimulation electrodes and an edge of the substrate.

In general, it is advantageous to maximize the tissue contact-area of the one or more return electrodes as this increase the efficiency of energy transfer to the tissue through the one or more stimulation electrodes.

According to a still further aspect of the present disclosure, a tissue stimulation system is provided wherein a further proximal return electrode is comprised in the second surface.

The second surface also comprises the one or more stimulation electrodes, so the space available for one or more return electrodes may be limited. There are fewer restrictions regarding the space available on the first surface for the one or more return electrodes. Having one or more proximal return electrode on both surfaces provides a high degree of flexibility for configuration.

According to another aspect of the present disclosure, a tissue stimulation system is provided wherein a plurality of stimulation electrodes is provided, each having one or more corresponding proximal return electrodes.

This allows stimulation to be provided at different positions along the longitudinal axis by predetermining and/or controlling the energy passing through one or more of the electrodes.

According to another further aspect of the present disclosure, there is provided a tissue stimulation system wherein the combined tissue contact-area of the one or more proximal return electrodes and the one or more distal return electrodes is no less than the tissue contact-area of the one or more stimulation electrodes.

In general, it is advantageous to maximize the tissue contact-area of the one or more return electrodes as this increase the efficiency of energy transfer to the tissue through the one or more stimulation electrodes.

BRIEF DESCRIPTION OF THE DRAWINGS

Features and advantages of some embodiments of the present invention, and the manner in which the same are accomplished, will become more readily apparent upon consideration of the following detailed description of the invention taken in conjunction with the accompanying drawings, which illustrate preferred and exemplary embodiments, and which are not necessarily drawn to scale, wherein.

DETAILED DESCRIPTION

In the following detailed description, numerous non-limiting specific details are given to assist in understanding this disclosure.

In general, stimulation systems described herein may comprise a stimulation energy source and an implantable end—the implantable end comprises one or more stimulation electrodes. "Implantable end" means that at least this section of the stimulation system is configured and arranged to be implanted. Optionally, one or more of the remaining sections of the stimulation systems may also be configured and arranged to be implanted.

Figure 1A:
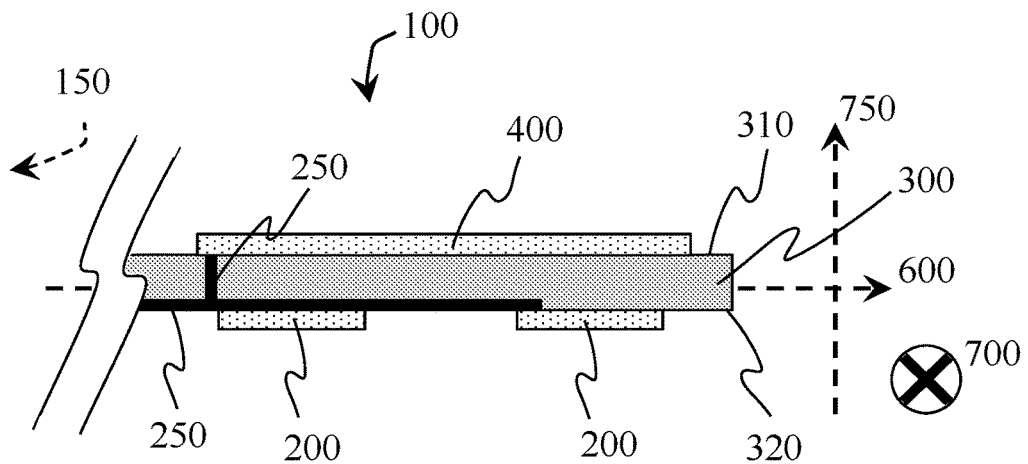
FIGS. 1A, 1B & 1C depict longitudinal cross-sections through a first embodiment of an implantable end (lead) of a stimulation system.
Figure 1B:
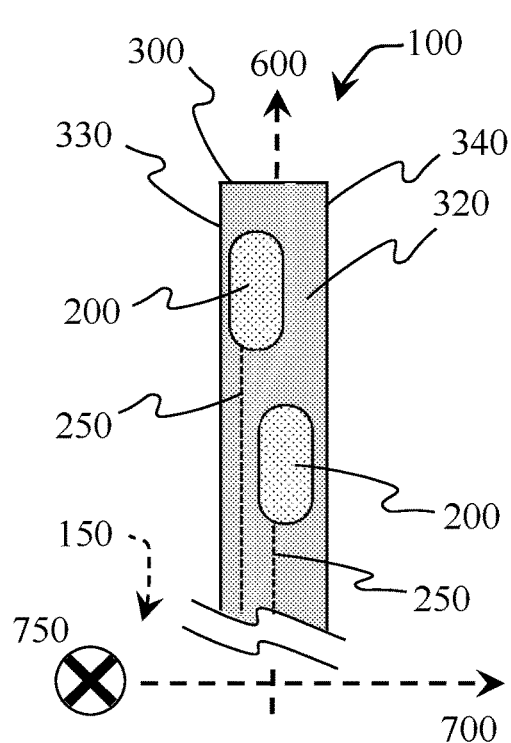
Figure 1C:
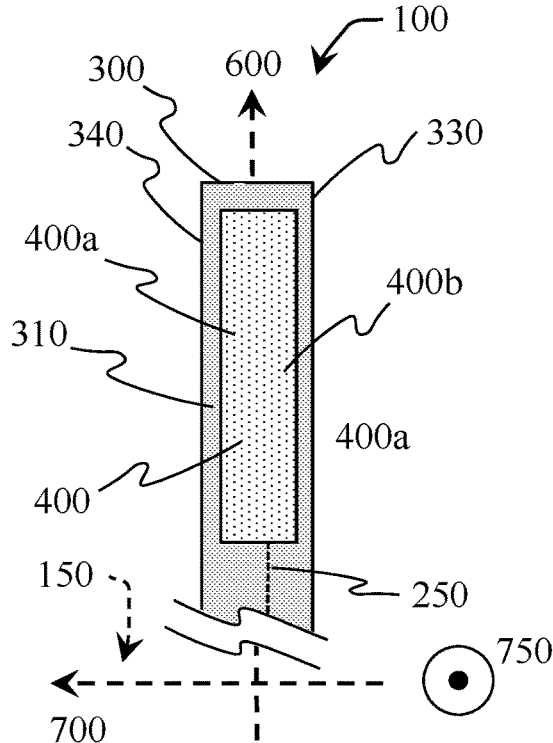

FIGS. 1A, 1B & 1C depict longitudinal cross-sections through a first embodiment 100 of an implantable end (lead) of a stimulation system 100, 150 comprising:
  an elongated substrate 300, disposed along a longitudinal axis 600, the substrate having a first 310 and second 320 surface disposed along substantially parallel transverse planes 600, 700. For substrates 300 with a degree of flexibility, the degree to which the first 310 and second 320 surface are along substantially parallel transverse planes 600, 700 may be determined by laying the substrate 300 on a substantially flat surface. As depicted, the first surface 310 lies in a plane comprising the longitudinal axis 600 and a first transverse axis 700—the first transverse axis 700 is substantially perpendicular to the longitudinal axis 600. As depicted, the plane of the first surface 310 is substantially perpendicular to the plane of the cross-section drawing (substantially perpendicular to the surface of the paper). The substrate 300 has a thickness or extent along a second transverse axis 750—this second transverse axis 750 is substantially perpendicular to both the longitudinal axis 600 and the first transverse axis 700—it lies in the plane of the drawing (along the surface of the paper) as depicted. The first surface 310 is depicted as an upper surface and the second surface 320 is depicted as a lower surface.

To clarify the different views, the axes are given nominal directions:
  the longitudinal axis 600 extends from the end comprising a stimulation energy source 150 on the left, to the end of the implantable end (the lead), depicted on the right of the page;
  the first transverse axis 700 extends into the page as depicted; and
  the second transverse axis 750 extends from bottom to top as depicted.

For example, the elongated substrate 300 may comprise an elastomeric implantable end composed of silicone rubber, or another biocompatible, durable polymer such as siloxane polymers, polydimethylsiloxanes, polyurethane, polyether urethane, polyetherurethane urea, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, polyethylene, and polyvinylacetate. Suitable examples of polymers, including LCP (Liquid Crystal Polymer), are described in "Polymers for Neural Implants", Hassler, Boretius, Stieglitz, Journal of Polymer Science: Part B Polymer Physics, 2011, 49, 18-33 (DOI 10.1002/polb.22169), In particular, Table 1 is included here as reference, depicting the properties of Polyimide (UBE U-Varnish-S), Parylene C (PCS Parylene C), PDMS (NuSil MED-1000), SU-8 (MicroChem SU-8 2000 & 3000 Series), and LCP (Vectra MT1300).

Flexible substrates 300 are also preferred as they follow the contours of the underlying anatomical features very closely. Very thin substrates 300 have the additional advantage that they have increased flexibility.

Preferably, the flexible substrate 300 comprises an LCP, Parylene and/or a Polyimide. LCPs are chemically and biologically stable thermoplastic polymers which allow for hermetic sensor modules having a small size and low moisture penetration.

Advantageously, an LCP may be thermoformed allowing complex shapes to be provided. Very thin and very flat sections of an LCP may be provided. For fine tuning of shapes, a suitable laser may also be used for cutting. For example, LCP substrates 300 with thicknesses (extent along the second transverse axis 750) in the range 50 microns (um) to 720 microns (um) may be used, preferably 100 microns (um) to 300 microns (um). For example, values of 150 um (micron), 100 um, 50 um, or 25 um may be provided. Similarly, substrate widths (extent along the first transverse axis 600) of 2 mm to 20 mm may be provided using LCP, for example.

At room temperature, thin LCP films have mechanical properties similar to steel. This is important as implantable substrates 300 must be strong enough to be implanted, strong enough to be removed (explanted) and strong enough to follow any movement of the anatomical feature and/or structure against which it is implanted.

LCP belongs to the polymer materials with the lowest permeability for gases and water. LCPs can be bonded to themselves, allowing multilayer constructions with a homogenous structure.

In contrast to LCPs, polyimides are thermoset polymers, which require adhesives for the construction of multilayer substrates. Polyimides are a thermoset polymer material with high temperature and flexural endurance.

An LCP may be used, for example, to provide a substrate having multilayers (not depicted) in other words, several layers of 25 um (micron) thickness. Electrical interconnections and/or interconnect layers may also be provided by metallization using techniques from the PCB (Printed Circuit Board) industry, such as metallization with a biocompatible metal such as gold, silver or platinum. Electroplating may be used. These electrical interconnections and/or interconnect layers may be used to provide electrical energy to any electrodes.

The implantable end of the system 100 depicted in FIG. 1 further comprises:
  one or more stimulation electrodes 200, comprised in the second surface 320 and configured to transmit energy, in use, to human or animal tissue (after implantation). In this example, it is electrical energy, and two stimulation electrodes 200 are depicted. Each stimulation electrode 200 has a longitudinal extent along the longitudinal axis 600 and a transverse extent along a first transverse axis 700, the first transverse axis 700 being substantially perpendicular to the longitudinal axis 600 and substantially parallel to the second surface 320.

"Comprised in the second surface" means that stimulation electrode 200 is relatively thin, and attached to the second surface 320. The electrode 200 may also be embedded in the second surface 320.

In general, one or more stimulation electrodes 200 may be provided. The number, dimensions and/or spacings of the stimulating electrodes 200 provided in the implantable end 100 may be selected and optimized depending on the treatment for example, if more than one electrode 200 is provided, each electrode 200 may provide a separate stimulation effect, a similar stimulation effect or a selection may be made of one or two electrodes 200 proximate the tissues where the effect is to be created. The electrodes 200 may comprise a conductive material such as gold, silver or platinum, iridium, and/or platinum/iridium alloys and/or oxides.

FIG. 1B depicts two stimulation electrodes 200, each elongated along the longitudinal axis 200. Although an oval cross-section is suggested in FIGS. 1A and 1B, any shape may be used, such a square, rectangular, triangular, polygonal, circular, elliptical, oval, and round. An elongated electrode (or strip electrode) as depicted in FIG. 9 may also be used.

The implantable end 100 of the system 100, 150 depicted in FIG. 1 further comprises:
  one or more interconnections 250, configured and arranged to provide the one or more stimulation electrodes 200 with electrical energy from a stimulation energy source 150; and
  one or more interconnections 250, configured and arranged to provide an electrical return for the one or more stimulation electrodes (200, 220) using one or more proximal return electrodes 400.

The one or more interconnections 250 may be disposed between the first 310 and second surface 320, comprised in the first surface 310, comprised in the second surface 320, or any combination thereof. In this case, they are depicted as being disposed between the first 310 and second surface 320.

They may comprise one or more conductors, such as a metal, formed as required for example, in one or more conductive: wire, strand, foil, lamina, plate, and/or sheet. They may be a substantially contiguous (one conductor) or comprise a plurality of conductors. In this, they are depicted as three wire-like conductors, encapsulated in the substrate 300, disposed along the longitudinal axis 600, two of which are connected to the two stimulation electrodes 200. The third wire-like conductor is connected to the one proximal return electrode 400 (described below in more detail) via a further wire-like conductor, disposed along the second transverse axis 750.

An interconnection 250 in the context of this disclosure is not configured or arranged to be, in use, in contact with human or animal tissue. For example, by embedding the one or more interconnections 250 in a low conductance or insulating substrate 300, such as LCP. Note that an interconnection 250 may be comprised in the first 310 or second surface 320 if it rendered low conductance and/or insulating by including one or more layers between the interconnection 250 and any human or animal tissue.

Additionally or alternatively, the substrate 300 may be a multilayer, comprising one or more electrical interconnection layers to provide the electrode 200 with electrical energy. In use, the electrical interconnections are connected to a source of electrical power (not depicted). If an LCP multilayer is used, the thickness (extent of the substrate 300 along the second transverse axis 750 or the perpendicular distance between the first surface 310 and the second surface 320) may be typically approximately 150 um (micron) in the sections with no electrodes 200 or interconnections, 250 um in the sections with an electrode 200, and 180 um in the sections with an electrical interconnection 250. If multilayers are used, electrical interconnection layers of 25 um (micron) may be used, for example.

The implantable end 100 of the system 100, 150 depicted in FIG. 1 further comprises:
  one or more proximal return electrodes 400 (in this case, one proximal return electrode 400), comprised in the first surface 310, disposed proximate the one or more stimulation electrodes 200 at substantially the same longitudinal disposition 600.

In the context of this disclosure, proximal is used to describe proximity to the one or more stimulation electrodes 200, comprised in the implantable end 100.

The one or more proximal return (or ground) electrodes 400 are configured to provide, in use, a corresponding electrical return for one or more stimulation electrodes 200. In other words, the electrical return 400 closes the electrical circuit. Any suitable configuration and arrangement may be provided. Additionally or alternatively, one or more return (ground) electrodes may be provided proximate the one or more stimulation electrodes 200, at the implantable end 100 of the system 100, 150.

In some descriptions of conventional stimulation devices, the return electrode may be referred to as an anode. Traditionally, this has been provided via the housing of an IPG (Implantable Pulse Generator). Stimulation electrodes may similarly be referred to as cathodes.

The one or more proximal return electrodes 400 may comprise a conductive material such as gold, silver, platinum, iridium, and/or platinum/iridium alloys and/or oxides.

Alternatively, the depicted proximal return electrode 400 may be functionally described as follows: it comprises two proximal return electrode regions 400a, 400b, electrically connected to each other, the two proximal return electrode regions 400a, 400b being disposed on opposing sides of the one or more stimulation electrode 200. In other words, if the device 100 was viewed in a transverse cross-section 600, 700 (substantially parallel to the first 310 and second 320 substantially planar transverse surfaces), the main regions 400a, 400b of the proximal return electrode 400 that influence the stimulation current density are disposed directly "above" the one or more stimulation electrodes 200 (but further along the second transverse axis 750). In other words, at substantially the same disposition along the first transverse axis 700 as the one or more stimulation electrodes 200. The regions 400a, 400b are disposed along the first transverse axis 700 approximately proximate (and approximately parallel to) opposing edges of the substrate 300.

The two proximal return electrode 400 regions a, b are comprised in a substantially contiguous proximal return electrode 400.

An end (or lead) 100 suitable for implanting may comprise, for example, 12 stimulation electrodes over a length of 15 cm. Each stimulation electrode may have dimensions in the order of 6 to 8 mm along the longitudinal axis 600 and 3 to 5 mm along the first transverse axis 700, so approximately 18 to 40 square mm ($mm^2$). If a strip of 4 mm wide (extent along the first transverse axis 700) is provided as a return electrode, then a length (extent along the longitudinal axis 600) of 4.5 to 10 mm also provides a tissue contact-area of 18 to 40 square mm ($mm^2$).

FIG. 1B depicts a view of the second surface 320 of the implantable end 100 depicted in FIG. 1A. In other words, the second surface 320 is depicted in the plane of the paper, lying along the longitudinal axis 600 (depicted from bottom to top) and in the first transverse axis 700 (depicted from left to right). The second transverse axis 750 extends into the page. This is the view facing the animal or human tissue which is stimulated (in use). The first surface 310 is not depicted in FIG. 1B, but lies at a higher position along the second transverse axis 750 (into the page), and is also substantially parallel to the plane of the drawing.

The substrate 300 extends along the first transverse axis 700 (considered the width of the implantable end 100 of the stimulation device) between two extents.

The implantable end 100 of the device may be implanted by first creating a tunnel and/or using an implantation tool.

The one or more proximal return electrodes 400 are depicted in FIGS. 1A and 1C, but not in FIG. 1B.

After implantation of the implantable end 100 of the system 100, 150, a source of stimulation energy may be configured and arranged to provide, in use, electrical energy to the one or more stimulation electrodes 200 with respect to the electrical return applied to the one or more return electrodes 400.

By providing one or more proximal return electrodes proximate the one or more stimulation electrodes at substantially the same longitudinal disposition, a substantially transverse electric field may be provided. It may then provide a more concentrated current density and distribution in directions approximately perpendicular to the longitudinal axis (transversely-oriented electric field). This provides an additional degree of configuration for stimulation systems and devices.

Figure 2A:
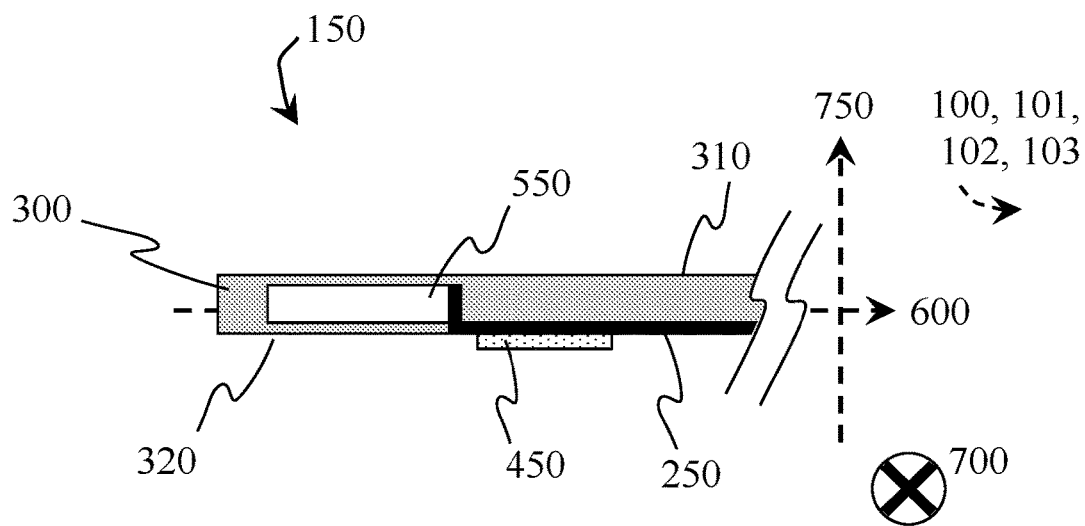
FIGS. 2A, 2B & 2C depict an example of a stimulation energy source.
Figure 2B:
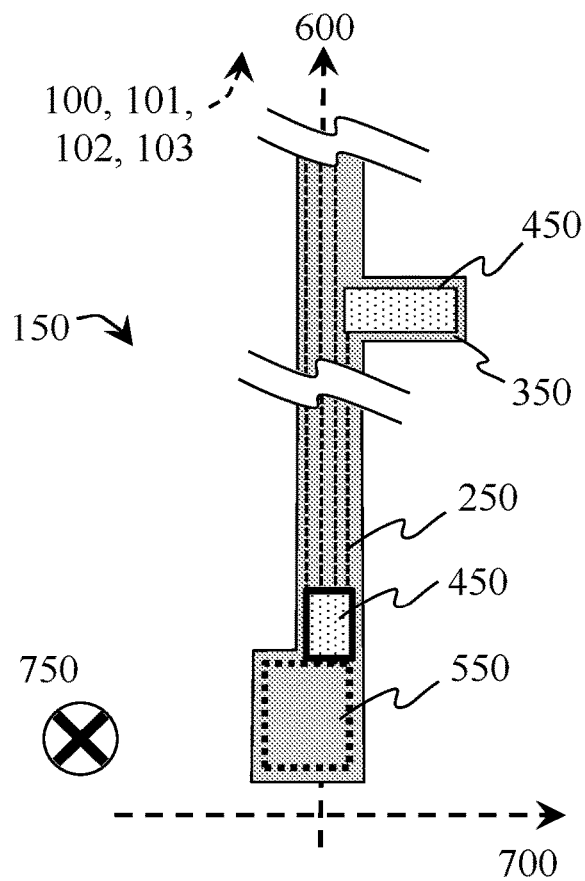
Figure 2C:
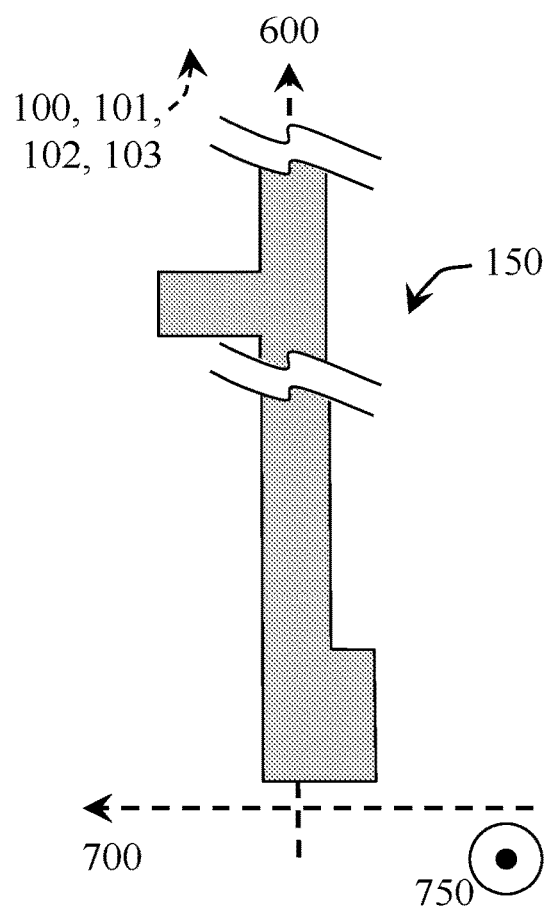

FIGS. 2A, 2B & 2C depict longitudinal cross-sections through an example of a stimulation energy source 150, suitable for use with any of the implantable ends described in this disclosure, including the first example 100 depicted in FIG. 1. Optionally, the stimulation energy source 150 may be configured and arranged to be implantable.

In this example, they are assumed to be comprised in the same substrate 300. The stimulation energy source 150 comprises analogous features to those depicted in FIG. 1:
the implantable end 100 comprises the same features as depicted in FIG. 1:
  the elongated substrate 300, disposed along the longitudinal axis 600, with the first 310 and second 320 surfaces;
  the first transverse axis 700 extending into the page as depicted, and the second transverse axis 750 extending from bottom to top as depicted;
  the longitudinal axis 600 extending from the stimulation energy source 150 end on the left, to the implantable end 100, towards the right of the page.

The dimensions of the substrate 300 (extent along the first transverse axis 700 or width, extent along the second transverse axis 750 or thickness) at the implantable 100 and energy source 150 ends are depicted as approximately the same. It is convenient if the device 100, 150 comprises the same substrate 300, allowing it to be made from a single piece of material this is advantageous if the implantable end 100 of the device is substantially completely implanted as this may reduce the risk of fluid ingress into the device.

The stimulation energy source 150 further comprises:
a pulse energy controller 550, configured and arranged to provide stimulation energy through the one or more stimulation electrodes 200 as one or more electrical pulses. This changes the electrical potential (or voltage) and/or current applied to the one or more stimulation electrodes 200. The pulse energy controller 550 may be connected to the one or more electrodes 200 through one or more interconnections 250.
one or more distal return (or ground) electrodes 450, configured and arranged to provide, in use, a corresponding electrical return for the one or more stimulation electrodes 200 which receive stimulation energy from the pulse energy controller 550. In other words, the electrical return 450 closes the electrical circuit. Any suitable configuration and arrangement may be provided—for example, as depicted, one distal return electrode 450 is comprised in the second surface 320, proximate the pulse energy controller 550. Additionally or alternatively, one or more distal return (ground) electrodes 450 may be comprised in the first surface 310. Additionally or alternatively, a further distal return electrode 450 may be provided between the energy source 150 and the implantable end 100, but closer to the energy source end 150. In this case, an additional substrate protrusion 350 is provided for the further distal ground electrode 450.

In the context of this disclosure, distal is used to describe proximity to the pulse energy controller 550, comprised in the stimulation energy source 150 and/or close to the energy source 150.

Preferably, the one or more distal return electrodes 450 that are to be actively used are comprised in a section of the device that is configured and arranged to be implantable. In addition, during use, the active one or more distal return electrodes 450 are preferably implanted so that they may provide a corresponding electrical return for the implanted one or more stimulation electrodes 200 that are active.

The one or more distal return electrodes 450 may comprise a conductive material such as gold, silver, platinum, iridium, and/or platinum/iridium alloys and/or oxides.

The stimulation energy source 150 further comprises:
  one or more interconnections 250, configured and arranged to connect the output of the pulse generator 550 to the one or more stimulation electrodes 200 such that electrical energy may be transferred. In FIG. 2B, three dashed longitudinal lines are used to represent interconnections 250 between the pulse energy controller 550 and the implantable end 100 one for each stimulation electrode 200 and one for the proximal return electrode 400.
  one or more interconnections 250, configured and arranged to provide an electrical return for the one or more stimulation electrodes 200, 220 using one or more distal return electrodes 450. In FIG. 2B, one dashed longitudinal line is used to represent interconnections 250 between the pulse energy controller 550 and the further distal return electrode 450 comprised in the substrate protrusion 350.

The functions comprised in the pulse energy controller 550, the separation into functional units, and the components used in each functional unit may be any suitable mix to perform the required functions. In terms of the invention, during stimulation operation, the pulse energy controller 550 transfers electrical energy to one or more stimulation electrodes 200 as one or more electrical stimulation pulses.

The one or more proximal return electrodes 400 are configured as a first part of the electrical return 400, 450 for the one or more stimulation electrodes 200; and the one or more distal return electrodes 450 are configured as a second part of the electrical return 400, 450 for the one or more stimulation electrodes 200.

So the electrical return comprises the first part, proximate the one or more stimulation electrodes 200 and the second part, distant from (distal) one or more stimulation electrodes.

The pulse energy controller 550 further comprises a ratio controller, configured and arranged to modify the electrical ratio of the first part (proximal) of the electrical return to the second part (distal). The ratio controller provides a convenient way to concentrate or diffuse the substantially transverse 700, 750 electric field.

The proximal:distal ratio may vary between 0:1 and 1:0. Expressed in percentages, this is 0%: 100% to 100%: 0%. When one of the parts of the electrical returns is approximately 0, it is substantially disabled and very similar to the situation where those types of electrodes are not connected (or are disconnected).

At 1:0, the electric field is stronger (more localized in the regions close to the stimulation electrodes). At 0:1, the electric field is weaker (more global, and distributed through the tissue between the proximal return electrodes 400 and the distal electrodes 450).

Stimulation electrodes 200, such as those depicted in FIG. 1C, may have, for example, a dimension along the longitudinal axis 600 (a longitudinal extent) on the order of 6 to 8 mm, with a pitch of 10 to 12 mm along the longitudinal axis.

An active proximal return electrode 400 is most preferably disposed at substantially the same longitudinal disposition as the corresponding active one or more stimulation electrodes 200.

Although less preferred, an active return electrode 400 may also be considered proximal if it is disposed within a distance of one stimulation electrode longitudinal extent (for example, 6 to 8 mm) from the corresponding active one or more stimulation electrodes 200.

Although even less preferred, an active return electrode 400 may also be considered proximal if it is disposed within a distance of two stimulation electrode longitudinal extents (for example, 12 to 16 mm) from the corresponding active one or more stimulation electrodes 200.

An active return electrode 450 may be considered distal if it is more than three stimulation electrode longitudinal extent (for example, 18 to 24 mm) from the corresponding one or more active stimulation electrodes 200.

US 2010/0057165 describes more than one return electrodes at different distances from one or more corresponding stimulation electrode. However, in the terms of the invention, these are proximal return electrodes comprised in the implantable end or paddle. It does not describe the combined use of a distal return electrode, comprised in the stimulation energy source, together with a proximal electrode using a predetermined ratio.

Figure 10A:
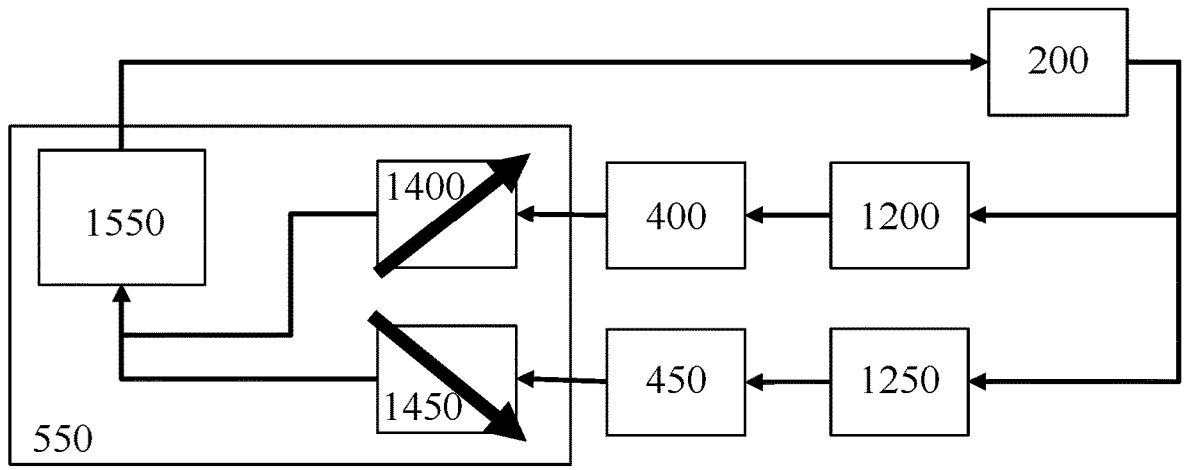
FIGS. 10A and 10B depict example of electrical paths through the patient body.

FIG. 10A depicts a simplified electrical diagram of the electrical energy paths through the patient body.

The electrical energy is provided as stimulation pulses from an energy source 1550 comprised in the pulse energy controller 550. The stimulation pulses are provided to one or more stimulation electrodes 200. Two main paths of stimulation current are created through the patient body:
- a proximal (local) path, from the one or more stimulation electrodes 200, through proximal resistive tissue 1200 to the one or more proximal return electrode 400, and returning back to the pulse energy controller 550;
- a distal (global) path, from the one or more stimulation electrodes 200, through distal resistive tissue 1250 to the one or more distal return electrode 450, and returning back to the pulse energy controller 550.

As depicted in FIG. 10A, the ratio controller may be implemented using:
- a proximal variable resistor 1400 connected between the one or more proximal return electrodes 400 and the electrical return of the pulse energy source 1550;

and
- a distal variable resistor 1450 connected between the one or more distal return electrodes 450 and the electrical return of the pulse energy source 1550.

By coupling together the variable adjustments of the proximal variable resistor 1400 and the distal variable resistor 1450, an increase in one of the resistance values may cause a decrease in resistance of the other, and vice-versa.

Additionally or alternatively, a fixed resistor may be used in one of the paths to adjust the ranges of ratios that may be controlled in this way.

One proximal path 1200, 400, 1400 is depicted in FIG. 10A—optionally, if more than one active proximal return electrode 400 is provided, more than one proximal path 1200, 400, 1400 may also be provided. They may be configured for operation together (in other words, more than one proximal return electrodes 400 connected electrically to the same proximal variable resistor 1400) or they may be configured to be operated separately (in other words, more than one proximal return electrode 400 connected electrically to more than one proximal variable resistor 1400). If configured to be operated separately, the ratios between different proximal paths may be adjusted—this may be advantageous as it may create a more complex distribution of field densities.

One distal path 1250, 450, 1450 is depicted in FIG. 10A—optionally, if more than one active distal return electrode 450 is provided, more than one distal path 1250, 450, 1450 may also be provided. They may be configured for operation together (in other words, more than one distal return electrodes 450 connected electrically to the same distal variable resistor 1450) or they may be configured to be operated separately (in other words, more than one distal return electrode 450 connected electrically to more than one distal variable resistor 1450). If configured to be operated separately, the ratios between different distal paths may be adjusted—this may be advantageous as it may create a more complex distribution of field densities.

The variable resistors 1400, 1450 may be linear. One or both may be non-linear. One or both may be logarithmic Additionally or alternatively, any non-linear or logarithmic behavior may be modified by adapting a user interface to make the adjustments seem more linear to the user. If a digital control system is used, then any required behavior may be provided.

The resistance of human tissue is typically in the range 0.8 kOhm to 1.2 kOhm. Human tissue is highly conductive. The resistance of the paths is less affected by the length of the path through tissue, and affected to a higher degree by the tissue contact area of the electrodes 200, 400.

Figure 10B:
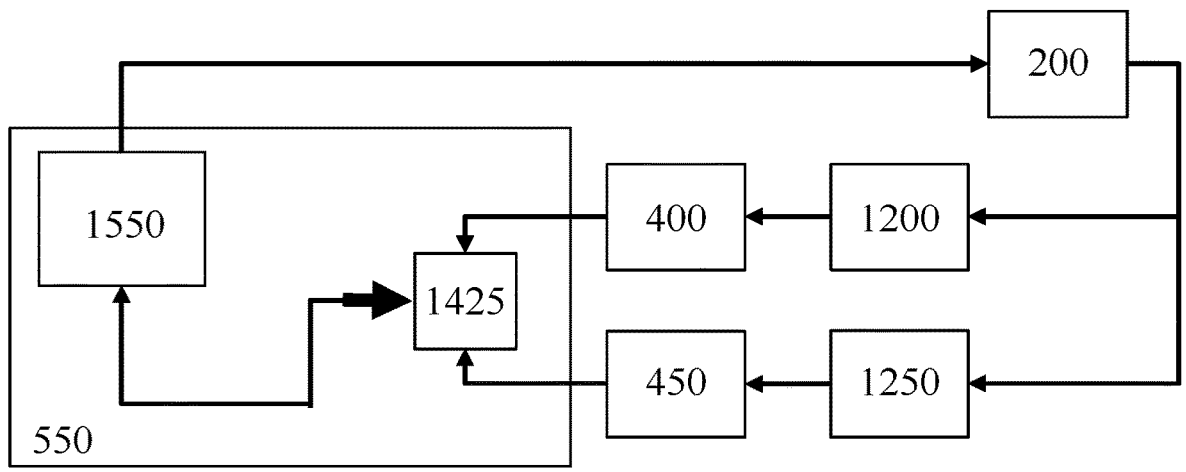

With pulses of 50 Hz (250 microseconds), typical values are:
- a proximal resistive tissue 1200 of 0.8 kOhm to 1.2 kOhm
- a proximal variable resistance 1400 of 0 to 2 kOhm
- a distal resistive tissue 1250 of 0.8 kOhm to 1.2 kOhm
- a distal variable resistance 1450 of 0 to 2 kOhm FIG. 10B depicts an alternative simplified electrical diagram of the electrical energy paths through the patient body.

It is the same as the circuit in FIG. 10A, except for the use of a rheostat 1425 instead of the variable resistors 1400 and 1450. One end of the rheostat 1425 is electrically connected to the proximal return electrode 400, and the other side of the rheostat 1425 is connected to the distal return electrode 450. The tap (or slider) is connected to the electrical return of the pulse energy source 1550.

By moving the tap (or slider), an increase in one of the path resistance values is provided at the same time as a decrease in resistance of the other path, and vice-versa.

Additionally or alternatively, a fixed resistor may be used in one of the paths to adjust the ranges of ratios that may be controlled in this way.

Variable resistors and/or rheostats 1400, 1425, 1450 may result in unwanted heat generation in the pulse energy controller 550.

Alternatively or additionally, a time multiplexer may be used to control the amount of time that each return path 1200, 400 and 1250, 450 is connected to the energy source. Such a configuration and arrangement reduces heat generation in the pulse energy controller 550. The longer that a path is connected within a particular period of time, the larger its contribution to electrical return. For example:

- connecting one of the return paths for a plurality (X) of stimulation pulses, then connecting the other return paths for a further plurality (Y) of stimulation pulses. The ratio is then determined by X:Y for the period X+Y. For example, a 1:1 ratio is possible by switching between pulses.
- connecting one of the return paths for a percentage (P) of a pulse width, then connecting the other return paths for a further percentage (Q) of the pulse width. The ratio is then determined by P:Q for the pulse width P+Q. For example, a 1:1 ratio is possible by switching halfway through each pulse.

Variable resistors 1400, 1450 may also be used in combination with a time multiplexer.

Alternatively or additionally, a plurality of (more than one) distal return paths 450, 1250 may be provided by providing more than one distal return electrode 450. When the tissue contact area of the return electrodes is maximised, the resistance 1250 through the patient tissue is mainly determined by the tissue contact surface area of the one or more distal return electrodes 450.

Alternatively or additionally, a plurality of (more than one) proximal return paths 400, 1200 may be provided by providing more than one proximal return electrode 400. When the tissue contact area of the return electrodes is maximised, the resistance 1200 through the patient tissue is mainly determined by the tissue contact surface area of the one or more proximal return electrodes 400.

Alternatively or additionally, the pulse energy controller 550 may comprise switches which may switch one or more of the plurality of return paths 400, 1200 and/or 450, 1250 into or out of the electrical return circuit to the energy source 1550. The time multiplexer described above may be further configured and arranged to switch between the plurality of return paths.

Additionally or alternatively, the one or more return electrodes 400, 450 may be increase or reduced in tissue contact area to predetermine the tissue contact area, which may influence the resistance of the return path 1200, 1250 through the body.

Additionally or alternatively, resistive elements may be comprised in the pulse energy controller 550, the one or more interconnections 250, and/or the one or more return electrode 400, 450 to predetermine differences in resistance between the return paths 400, 1200 and 450, 1250

Figure 4A:
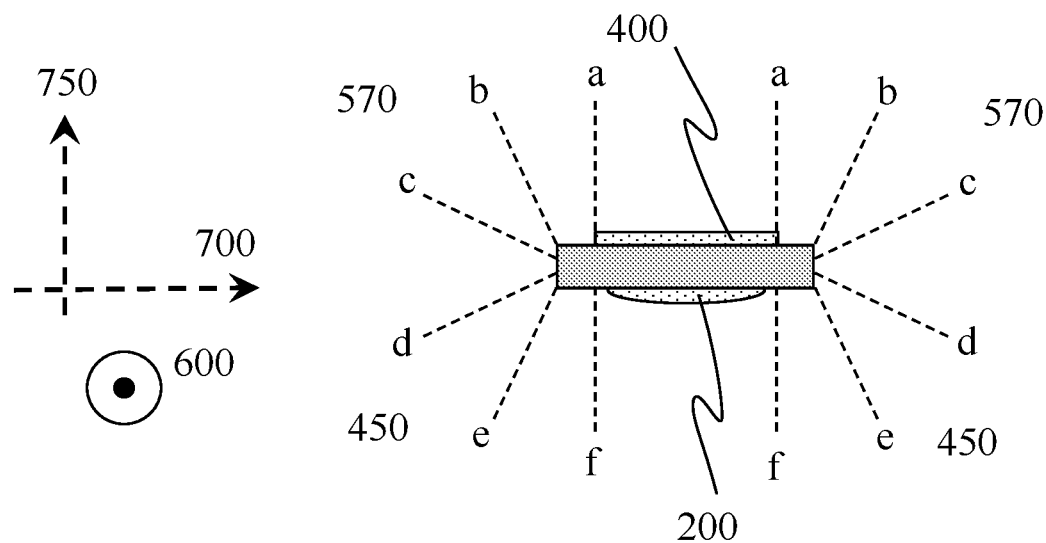
FIGS. 4A & 4B depict examples of how the electric field may be configured to vary the strength of the field close to the electrodes.
Figure 4B:
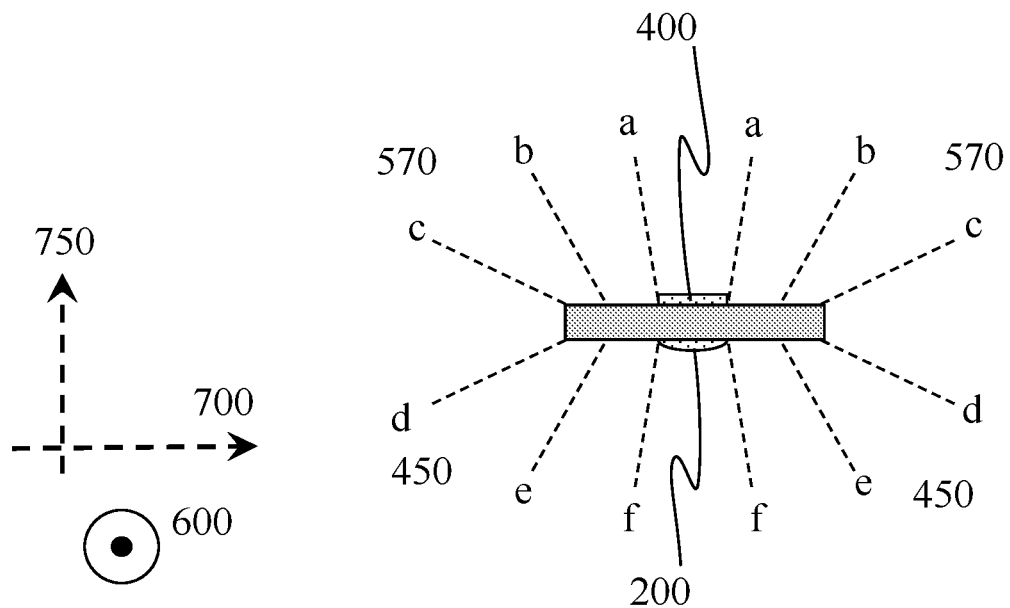

FIGS. 4A & 4B depict examples of how the electric field may be configured to vary the strength of the field close to the electrodes. FIG. 4A & FIG. 4B depict transverse cross-sections in the plane comprising the first transverse axis 700 and the second transverse axis 750 through a modified version of the electrodes depicted in FIGS. 1A, 1B and 1C. As viewed, the longitudinal axis 600 is perpendicular to the plane of the drawing (or the plane of the paper), and the direction is emerging. In other words, the transverse cross-section is viewed from an implantable end 100 looking towards an energy source 150 end.

One or more proximal return electrodes 400 are provided, comprised in the first surface 310. One or more stimulation electrodes 200 are provided, comprised in the second surface 320.

A corresponding proximal return electrode 400 and a stimulation electrode 200 are depicted. The proximal return electrode 400 is configured as a return (for example, a ground or 0V) for the stimulation electrode 200—if a positive voltage is applied to stimulation electrode 200, an electric field may be provided, in use, in the region between the stimulation electrode 200 and the proximal return electrode 400. Examples of lines of equipotential 570a to 570f are also depicted—the first equipotential 570a approximately coincides with the edges of the transverse extent 700 of the proximal return electrode 400. This is approximately the same potential as the proximal return electrode 400, here (for example) ground or 0V.

The last equipotential 570f approximately coincides with the edges of the transverse extent 700 of the stimulation electrode 200. This is approximately the same potential as the stimulation electrode 200.

Between the first 570a and last 570f equipotential lines, intermediate equipotential lines 570b to 570e are depicted—the distance between the equipotential lines 570 increases linearly over the distance "around" the substrate from the transverse edge 700 of the proximal return electrode 400 to the transverse edge 700 of the stimulation electrode 200.

For example, if 5V is applied to the stimulation electrode 200, and the proximal return electrode 400 is configured as ground (0V), then the approximate potential at each equipotential line 570 is 570a at 0V, 570b at 1V, 570c at 2V, 570d at 3V, 570e at 4V and 570f at 5V.

The transverse disposition 700 of the stimulation electrode 200 and the proximal return electrode 400 are approximately the same, providing a substantially symmetrical electrical field.

The extent along the first transverse axis 700 (width) of the corresponding return 400 and stimulation 200 electrodes is larger in FIG. 4A than in FIG. 4B. The first equipotential 570a is substantially disposed at the transverse edge 700 of the proximal return electrode 400 and the last equipotential 570f is substantially disposed at the transverse edge 700 of the stimulation electrode 200. The electrical field is provided between these two edges, "around" the substrate—the disposition difference along the first transverse axis 700 and/or the second transverse axis 750 determine the derivative of the potential over the distance—the closer the edges, the more local (the stronger) the electric field.

In addition, although not depicted in FIGS. 4A and 4B, the relative disposition along the longitudinal axis 600 of the edges also determines the longitudinal disposition of the electric field.

Although depicted as substantially symmetrical, the transverse positions of the proximal return 400 and stimulation 200 electrodes may be asymmetrical to provide a more asymmetrical electric field.

As depicted, the transverse extent 700 of the proximal return electrode 400 is less than the transverse extent 700 of the substrate. By making the transverse extents 700 more similar and optionally equal, the first equipotential 570a then approximately coincides with the edges of the transverse extent 700 of the substrate.

The devices 100, 101, 102, 103, 104, 105, 106 may further comprise one or more (conventional) stimulation electrodes not having a corresponding proximal return electrode.

Any of the proximal return electrode configurations 400, 401, 402, 403 disclosed herein may be combined with any of the stimulation electrode configurations 200, 220 disclosed.

From US 2011/0093043 A1, it is known to operate a stimulation device using a combination of return electrodes at different separations from the one or more stimulation electrodes. Although, substantially transverse fields may be created, as depicted in FIG. 20 and explained in the corresponding part of the description, the device requires two implantable electrode ends to create a substantially transverse field. This is because the proximal return electrode is not at substantially the same longitudinal disposition in the implantable end as the corresponding stimulation electrode the lead comprises a sequence of electrodes, some of which may be configured as return electrodes, which creates a substantially longitudinal field. In addition, the return electrode (or anode) may be provided via the housing of the Implantable Pulse Generator (IPG).

In the embodiments described in this disclosure, the use of an elongated substrate 300 with stimulation electrodes at substantially the same longitudinal disposition as the one or more proximal return electrodes means that a substantially transverse field may be created using only one lead. When using implanted leads (implantable ends comprising one or more electrodes), a reduction in the number of leads is advantageous.

This may be provided by a tissue stimulation system 100, 101, 102, 103, 150 comprising:
- an elongated substrate 300, 350, disposed along a longitudinal axis 600, the substrate having a first 310 and second 320 surface disposed along substantially parallel transverse planes 600, 700, the substrate 300, 350 further comprising:
  - one or more stimulation electrodes 200, 220, comprised in the second surface 320 and configured to transmit energy, in use, to human or animal tissue; and
  - one or more proximal return electrodes 400, 401, 402, 403, comprised in the first surface 310 or second surface 320, disposed proximate the one or more stimulation electrodes 200, 220 at substantially the same longitudinal disposition 600;
- the stimulation system further comprising:
- a pulse energy controller 550, configured and arranged to transfer electrical energy, during use, as one or more electrical stimulation pulses to the one or more stimulation electrodes 200, 220 with respect to an electrical return 400;

wherein:
the one or more proximal return electrodes 400, 401, 402, 403 are configured as the electrical return 400 for the one or more stimulation electrodes 200, 220.

In addition, in the embodiments in this disclosure, the geometric relationships between the one or more stimulation electrodes may be predetermined to a high degree, and are less dependent on the dispositions after implantation. Instead of relying on a distal return electrode that is at least tens of centimeters away (in US 2011/0093043 A1, use is made of the IPG housing), the embodiments in this disclosure use one or more distal return electrodes 450 more than three stimulation electrode longitudinal extents (for example, 18 to 24 mm) from the corresponding one or more active stimulation electrodes 200. This may improve control of the field density. Additionally, it may also reduce energy loss through the return paths.

As the resistance is mainly dependent on the tissue contact areas of the return electrodes 400, 450, the embodiments in this disclosure may provide return path resistances which may be predetermined to a high degree.

Figure 3A:
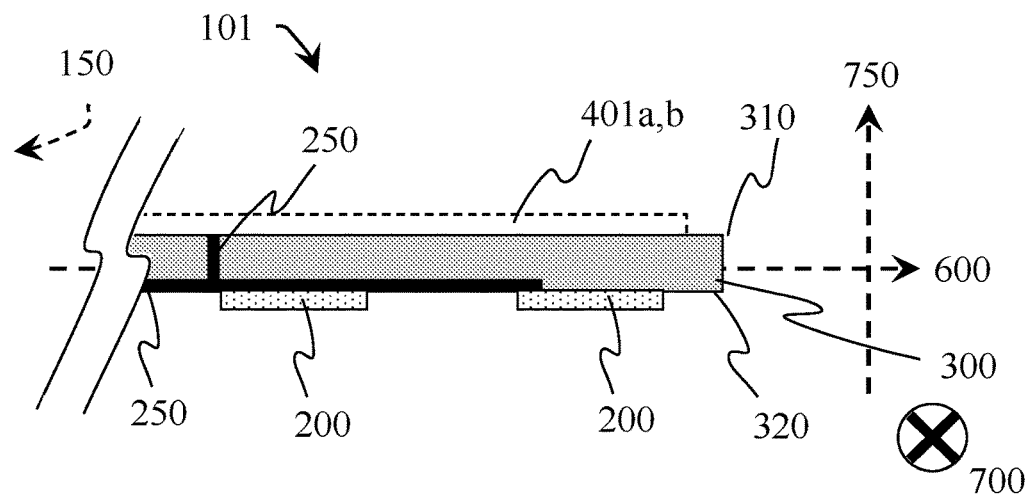
FIGS. 3A, 3B & 3C depict longitudinal cross-sections through a second embodiment of an implantable end (lead) of a stimulation system.
Figure 3B:
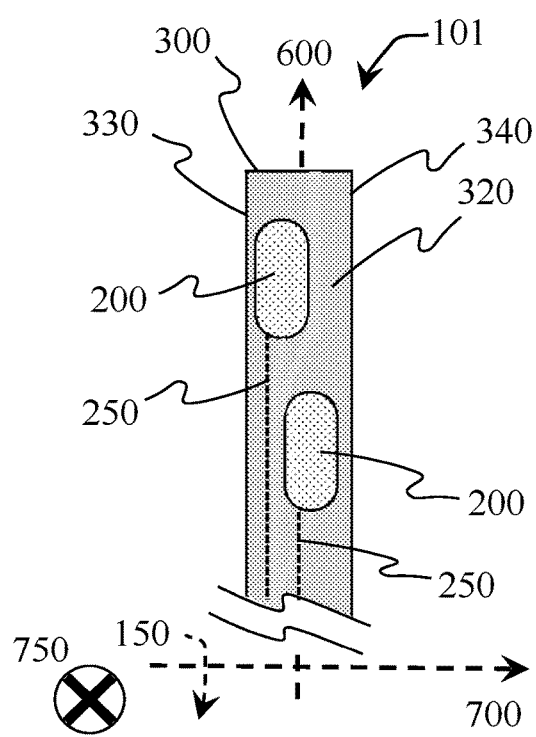
Figure 3C:
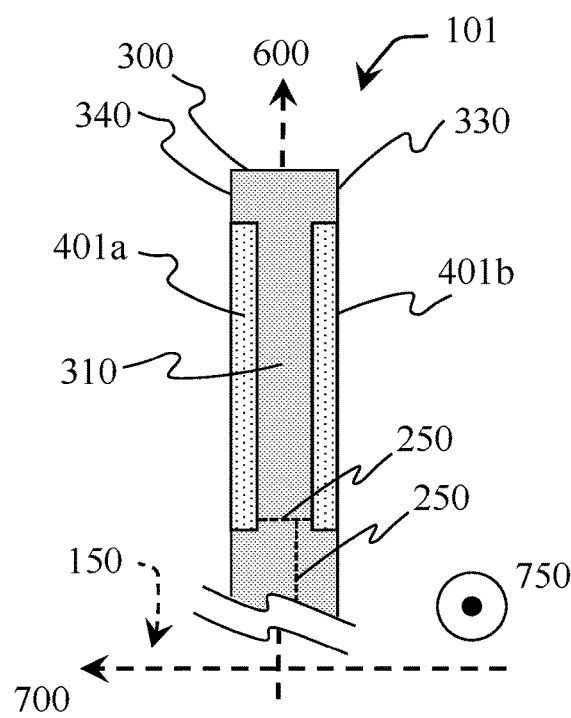

FIGS. 3A, 3B and 3C depict a second embodiment of an implantable end 101. It is the same as the first embodiment 100, depicted in FIG. 1 except:
- the proximal return electrode 401 similarly comprises two electrode regions 401a, 401b, electrically connected to each other, where each region comprises an electrode region. In FIG. 1, the two electrode regions 400a, 400b are comprised in a substantially contiguous proximal return electrode 400. Here, in FIG. 3, they are two non-contiguous electrode regions a, b, electrically connected to each other; and each return electrode region a, b is separated at least partially along the first transverse axis 700 from the one or more stimulation electrodes 200 by an electrical insulator, in this case the substrate material 300.
- the electrical connection between the two non-contiguous proximal return electrode regions 401a, 401b is made through one or more interconnections 250.

Similar to the return electrode 400 depicted in FIG. 1, the longitudinal 600 extent of the electrode regions 401a, 401b in FIG. 3 are approximately the same as the longitudinal 600 extent of the corresponding one or more stimulation electrodes 200.

The electrode regions 401a, 401b are least partially disposed along the first transverse axis 700 on opposite sides of the lower stimulation electrode 200. In other words, if the device 101 was viewed in a transverse cross-section 600, 700 (substantially parallel to the first 310 and second 320 substantially planar transverse surfaces), the regions 401a, 401b of the proximal return electrode 401 that influence the stimulation current density are disposed directly "above" (further along the second transverse axis 750) the transverse edges of the one or more stimulation electrode 200.

Figure 8A:
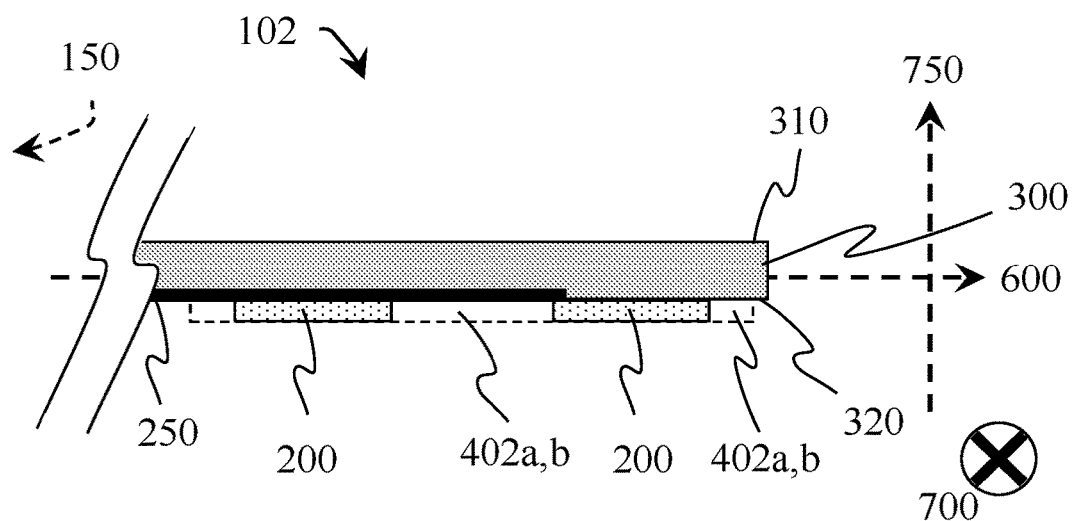
FIGS. 8A, 8B & 8C depict longitudinal cross-sections through a second embodiment of an implantable end (lead) of a stimulation system.
Figures 8B, 8C:
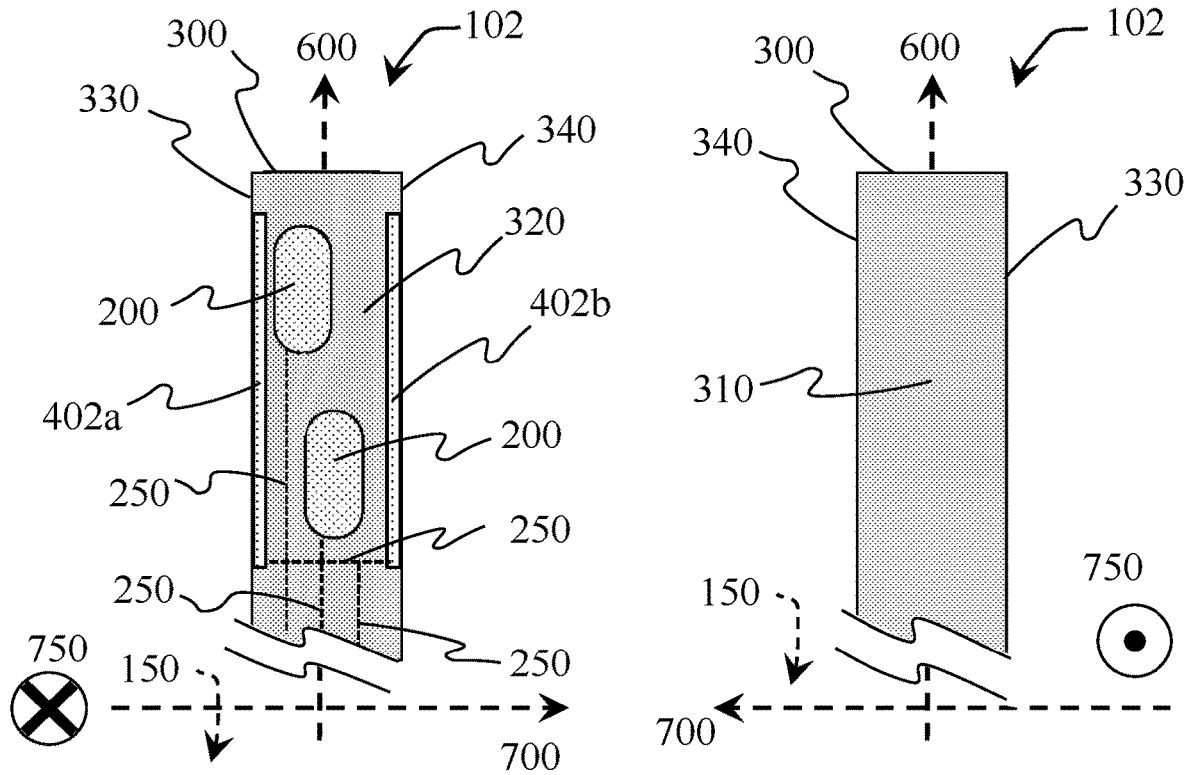

FIGS. 8A, 8B and 8C depict a third embodiment of an implantable end 102. It is the same as the second embodiment 101, depicted in FIG. 3 except:
- as depicted in FIG. 8C, no proximal electrode is comprised in the first surface 310
- a proximal return electrode 402 is provided, comprised in the second surface 320 and comprising two electrode regions 402a, 402b as two non-contiguous electrode regions 402a, 402b, electrically connected to each other through one or more interconnections 250, and configured to provide, in use, a corresponding proximal electrical return 402 for the one or more stimulation electrodes 200.

As in FIG. 3, this proximal return electrode 402 has a longitudinal 600 extent which approximates the longitudinal 600 extent of the one or more stimulation electrodes 200.

The regions 402a, 402b providing the corresponding proximal electrical return are at approximately the same longitudinal disposition 600 as their corresponding one or more stimulation electrodes 200.

Similar to proximal return electrode 401 in FIG. 3, the two electrode regions 402a, 402b of the proximal return electrode 402 are disposed on opposing sides of the one or more stimulation electrode 200. Also each return electrode region 402a, 402b is separated at least partially along the first transverse axis 700 from the one or more stimulation electrodes 200 by an electrical insulator.

Figure 9A:
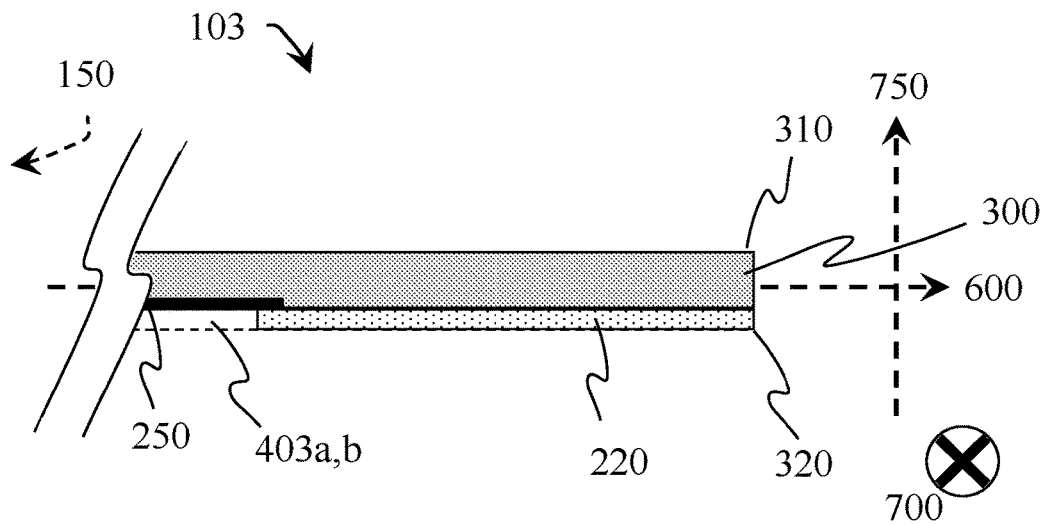
FIGS. 9A, 9B & 9C depict longitudinal cross-sections through a second embodiment of an implantable end (lead) of a stimulation system.
Figures 9B, 9C:
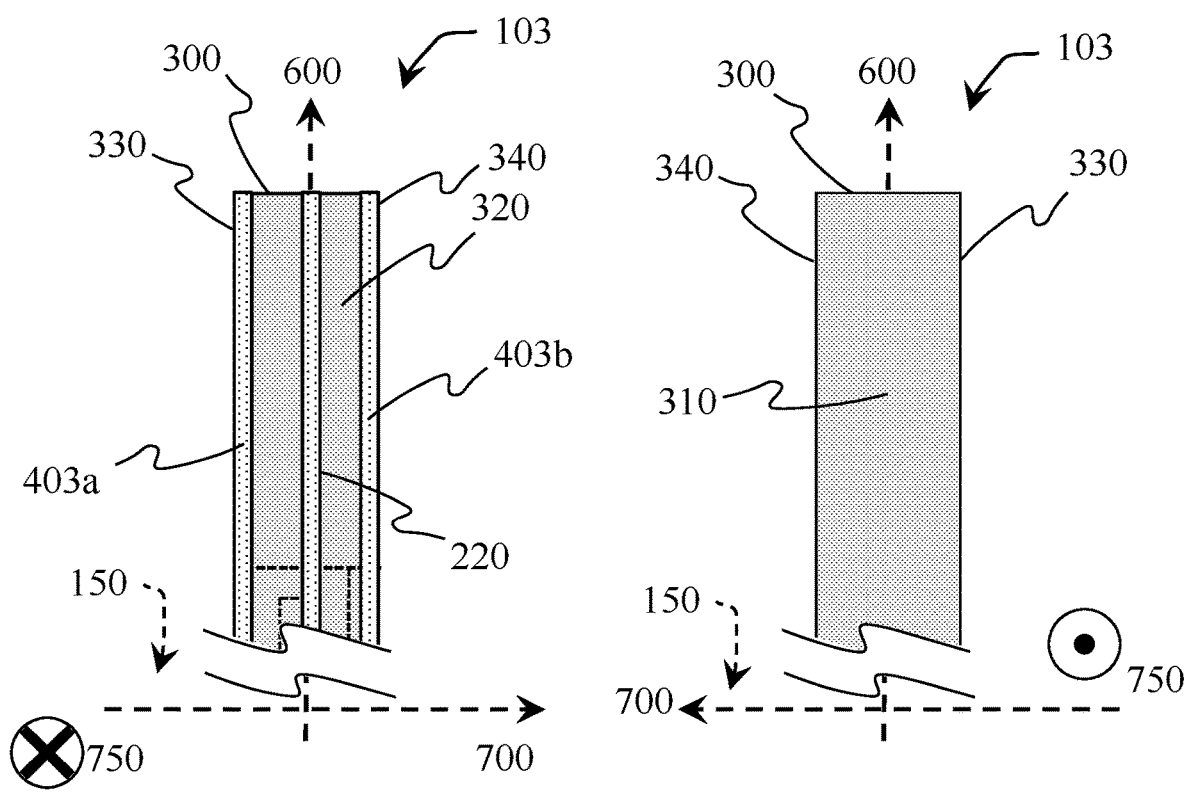

FIGS. 9A, 9B & 9C depict a longitudinal cross-section through an implantable end of a fourth embodiment 103. It is the same as the third embodiment 102, depicted in FIG. 8 except:

a stimulation electrode 220 is provided which is elongated along the longitudinal axis 600.

As in FIG. 8, the proximal return electrode 403 comprises two electrode regions 403a, 403b electrically connected to each other, through one or more interconnections 250, and configured to provide, in use, a corresponding electrical return for the stimulation electrode 220.

The two electrode regions 403a, 403b are elongated along the longitudinal axis 600, and disposed on opposing sides of the stimulation electrode 220, each electrode region 403a, 403b being separated from the stimulation electrode 220 by an electrical insulator (in this case, a separation between the conducting return electrode 403ab and the conducting stimulation electrode 220 which have been applied to a very low conducting (and/or very high resistant) substrate 300). Typically, the separation will be in the range 1 to 2 mm. Less than 1 mm may also be used, although it may be necessary to compensate for parasitic capacitance.

In general, one or more stimulation electrodes 220 may be provided. The number, dimensions and/or spacings of the stimulating electrodes 220 may be selected and optimized depending on the treatment—for example, if more than one electrode 220 is provided, each electrode 220 may provide a separate stimulation effect, a similar stimulation effect or a selection may be made of one or two electrodes 220 proximate the tissues where the effect is to be created. The electrodes 220 may comprise a conductive material such as gold, silver, platinum, iridium, and/or platinum/iridium alloys and/or oxides.

Although a rectangular cross-section is suggested in FIGS. 9A and 9B, any shape may be used, such a square, rectangular, triangular, polygonal, circular, elliptical, oval, and round. Typically, an elongated electrode 220 is used to provide stimulation energy along the entire extent—this is advantageous if the position of nerves to be stimulated is difficult to determine precisely.

In practice, the disposition and path of the nerve pathways vary from person-to-person, and it can happen that after implantation, a stimulation device may not function correctly due to misalignment. However, by using an elongated electrode 220, implanted at a significant angle (in some cases, approximately perpendicular), alignment becomes less critical—there is an increased chance that the elongated electrode 220 crosses a point in one or more nerve pathways, and the device 106 may be used to stimulate that nerve pathway.

In general, the combined active tissue contact-area of the return electrodes 400, 401, 402, 403, 450 is preferably equal to or more than the active tissue contact area contact-area of the one or more stimulation electrodes 200, 220. The tissue contact-areas to be considered are not the total contact areas, but the contact areas configured to be active during use—typically, this will be the whole (or a large proportion) of the return electrodes 400, 401, 402, 403, 450, and one or more stimulation electrodes 200, 220.

The stimulation electrode 220 may be selected to provide tissue stimulation at a particular disposition—two or more stimulation electrodes 220 may be made active if stimulation over a larger area is required and/or at a disposition between the active electrodes 220.

In general, the ratio between the tissue contact areas does not need to be determined exactly—they are preferably of a similar order of magnitude. For example, it may be sufficient if the combined active tissue contact area of the one or more return electrodes is equal to or more than 70% to 100% of the active tissue contact area of the one or more stimulation electrodes 200, 220.

An implantable device with an end (or lead) suitable for implant may comprise, for example, 12 stimulation electrodes over a length of 15 cm. A stimulation electrode may have dimensions on the order of 6 to 8 mm along the longitudinal axis 600 and 3 to 5 mm along the first transverse axis 700, so approximately 18 to 40 square mm (mm2) If a strip of 4 mm wide (extent along the first transverse axis 700) is provided as a return electrode, then a length (extent along the longitudinal axis 600) of 4.5 to 10 mm also provides a tissue contact-area of 18 to 40 square mm (mm2) The electric field is more concentrated between the strip (elongated electrode) and the corresponding stimulation electrode 200, 220.

Figure 5:
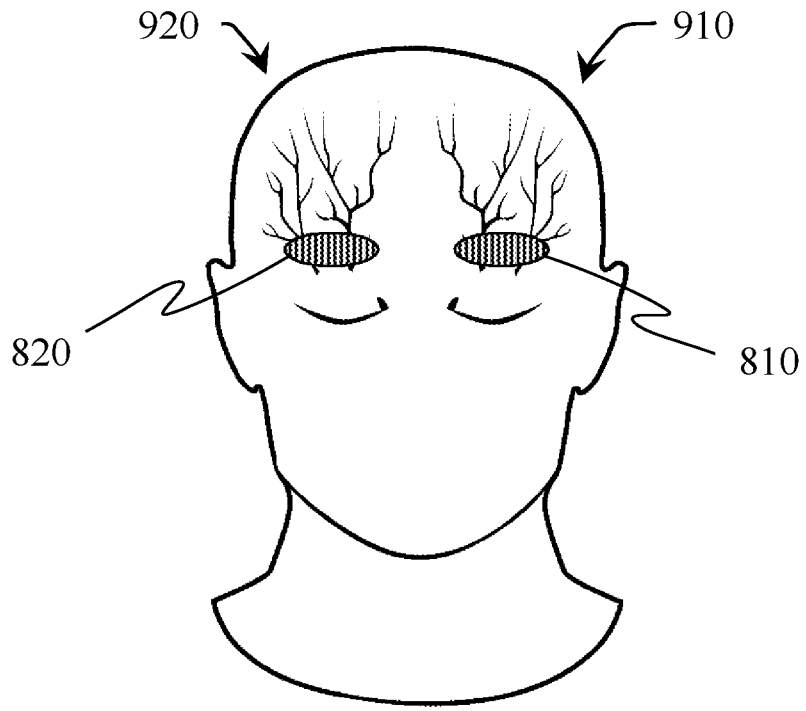
FIG. 5 and FIG. 6 depict examples of nerves that may be stimulated to treat headaches.
Figure 6:
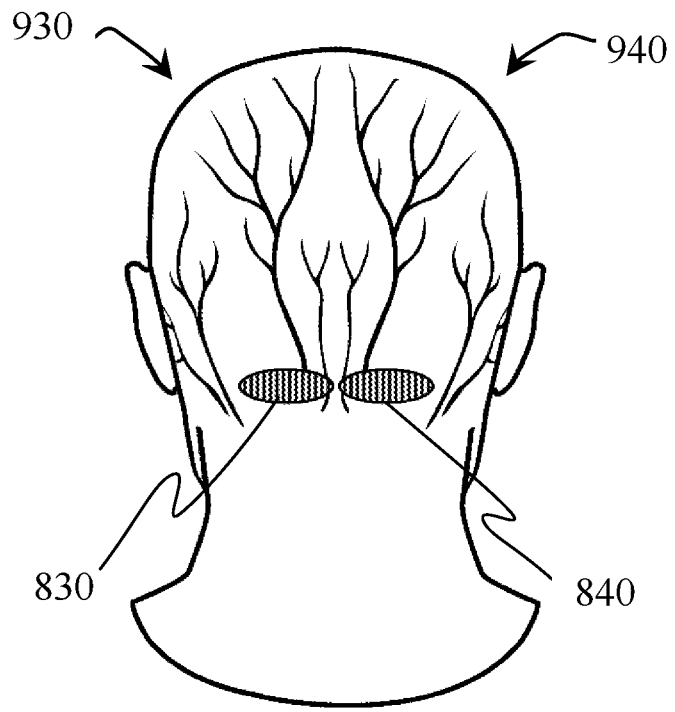

FIG. 5 and FIG. 6 depict examples of nerves that may be stimulated using a suitably configured implantable ends 100, 101, 102, 103 to provide neurostimulation to treat, for example, headaches or primary headaches. Providing suitably configured proximal return electrodes 400 means that the stimulation current density in substantially transverse directions 700, 750 may be increased, providing an improved stimulation along a longitudinal axis of one or more nerves or nerve branches.

FIG. 5 depicts the left supraorbital nerve 910 and right supraorbital nerve 920 which may be electrically stimulated using a suitably configured device. FIG. 6 depicts the left greater occipital nerve 930 and right greater occipital nerve 940 which may also be electrically stimulated using a suitably configured device.

Depending on the size of the region to be stimulated and the dimensions of the part of the device to be implanted, a suitable location is determined to provide the electrical stimulation required for the treatment. Approximate implant locations for the distal part of the stimulation device comprising stimulation devices 100, 101, 102, 103 are depicted as regions:

location 810 for left supraorbital stimulation and location 820 for right supraorbital stimulation for treating chronic headache such as migraine and cluster.

location 830 for left occipital stimulation and location 840 for right occipital stimulation for treating chronic headache such as migraine, cluster, and occipital neuralgia.

In many cases, these will be the approximate locations 810, 820, 830, 840 for the implantable device 100, 101, 102, 103.

For each implant location, 810, 820, 830, 840 a separate stimulation system may be used. Where implant locations 810, 820, 830, 840 are close together, or even overlapping, a single stimulation system may be configured to stimulate at more than one implant location 810, 820, 830, 840.

A plurality of stimulation devices 100, 101, 102, 103 may be operated separately, simultaneously, sequentially or any combination thereof to provide the required treatment.

Figure 7:
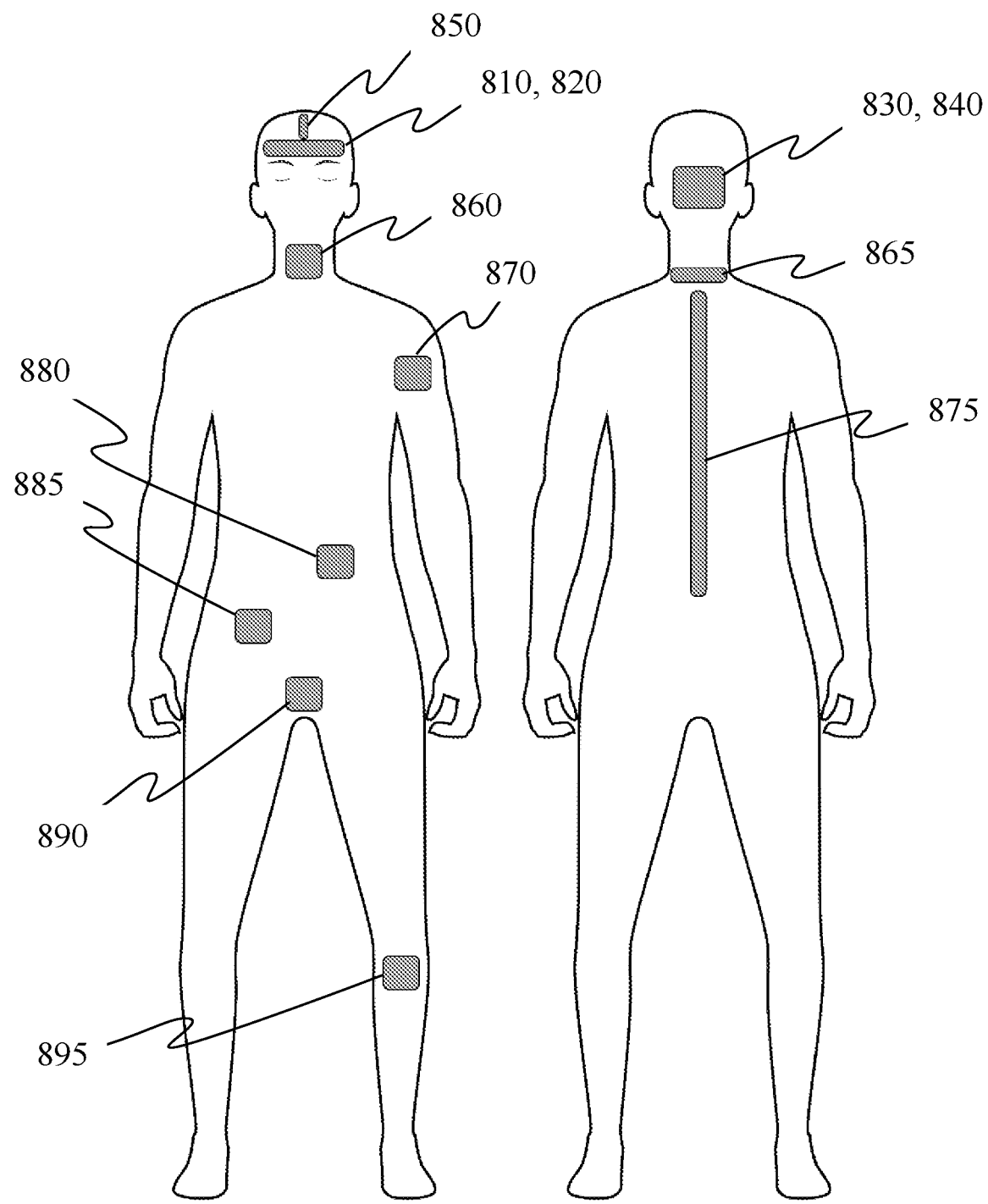
FIG. 7 depicts examples of nerves that may be stimulated for other treatments.

FIG. 7 depicts further examples of nerves that may be stimulated using a suitably configured improved implantable device 100, 101, 102, 103 to provide neurostimulation to treat other conditions. As in FIGS. 5 and 6, the ability to increase the stimulation current density in transverse directions 700 improves the stimulation along a longitudinal axis of the nerve or nerve branches. The locations depicted in FIG. 5 and FIG. 6 (810, 820, 830, 840) are also depicted in FIG. 7.

Depending on the size of the region to be stimulated and the dimensions of the part of the device to be implanted, a suitable location is determined to provide the electrical stimulation required for the treatment. Approximate implant locations for the part of the stimulation device comprising stimulation electrodes are depicted as regions:

location 810 for cortical stimulation for treating epilepsy;

location 850 for deep brain stimulation for tremor control treatment in Parkinson's disease patients; treating dystonia, obesity, essential tremor, depression, epilepsy, obsessive compulsive disorder, Alzheimer's, anxiety, bulimia, tinnitus, traumatic brain injury, Tourette's, sleep disorders, autism, bipolar; and stroke recovery;

location 860 for vagus nerve stimulation for treating epilepsy, depression, anxiety, bulimia, obesity, tinnitus, obsessive compulsive disorder and heart failure;

location 860 for carotid artery or carotid sinus stimulation for treating hypertension;

location 860 for hypoglossal & phrenic nerve stimulation for treating sleep apnea;

location 865 for cerebral spinal cord stimulation for treating chronic neck pain;

location 870 for peripheral nerve stimulation for treating limb pain, migraines, extremity pain;

location 875 for spinal cord stimulation for treating chronic lower back pain, angina, asthma, pain in general;

location 880 for gastric stimulation for treatment of obesity, bulimia, interstitial cystitis;

location 885 for sacral & pudendal nerve stimulation for treatment of interstitial cystitis;

location 885 for sacral nerve stimulation for treatment of urinary incontinence, fecal incontinence;

location 890 for sacral neuromodulation for bladder control treatment; and location 895 for fibular nerve stimulation for treating gait or footdrop.

Other condition that may be treated include gastroesophageal reflux disease and inflammatory diseases.

The descriptions thereof herein should not be understood to prescribe a fixed order of performing the method steps described therein. Rather the method steps may be performed in any order that is practicable. Similarly, the examples are used to explain the algorithm, and are not intended to represent the only implementations of these algorithms—the person skilled in the art will be able to conceive many different ways to achieve the same functionality as provided by the embodiments described herein.

In general, for any of the configurations described and depicted in this disclosure, any electrode 200, 400 may be connected as either a stimulating 200 or return electrode 400. This may be advantageous if it is uncertain whether the implantable end is above or below the targeted tissue—for example, above or below a nerve.

Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

For example, a method of controlling pulse energy of a tissue stimulation system 100, 101, 102, 103, 150 may be provided, the system comprising an implantable end 100, 101, 102, 103 and a stimulation energy source 150, the implantable end 100, 101, 102, 103 comprising:
an elongated substrate 300, 350, disposed along a longitudinal axis 600, the substrate having a first 310 and second 320 surface disposed along substantially parallel transverse planes 600, 700;
one or more stimulation electrodes 200, 220, comprised in the second surface 320; and
one or more proximal return electrodes 400, 401, 402, 403, comprised in the first surface 310 or second surface 320, disposed proximate the one or more stimulation electrodes 200, 220;

the stimulation energy source 150 comprising:
one or more distal return electrodes 450, disposed distantly from the one or more stimulation electrodes 200, 220; and
a pulse energy controller 550 comprising a ratio controller;

the tissue stimulation system 100, 101, 102, 103, 150 further comprising:
one or more interconnections 250 between the implantable end 100, 101, 102, 103 and a stimulation energy source 150;

the method comprising:
configuring the one or more stimulation electrodes 200, 220 to transmit energy, in use, to human or animal tissue;
configuring and arranging the output of the pulse energy controller 550 to connect to the one or more stimulation electrodes 200 whereby electrical energy may be transferred, during use, as one or more electrical stimulation pulses to the one or more stimulation electrodes 200, 220 with respect to an electrical return 400, 450;
configuring the one or more proximal return electrodes 400, 401, 402, 403 as a first part of the electrical return 400, 450 for the one or more stimulation electrodes 200, 220;
configuring the one or more distal return electrodes 450 as a second part of the electrical return 400, 450 for the one or more stimulation electrodes 200, 220; and
configuring and arranging the ratio controller to modify the electrical potential and/or current ratio of the first part to the second part.

For example, the return electrode embodiments may be implemented using one or more stimulation electrodes described in this disclosure. Examples of the implementation include F1, F2, F3, F4 or F5:

F.1 An implantable stimulation device comprising:
an elongated substrate 300, disposed along a longitudinal axis 600, the substrate having a first 310 and second 320 surface disposed along substantially parallel transverse planes 600, 700, the substrate 300 further comprising:
a stimulation electrode 200, 220, comprised in the second surface 320 and configured to transmit energy, in use, to human or animal tissue, the stimulation electrode 200, 220 having a longitudinal extent along the longitudinal axis 600 and a transverse extent along a first transverse axis 700, the transverse axis 700 being substantially perpendicular to the longitudinal axis 600 and substantially parallel to the second surface 320; and
a return electrode 400, 401, 402, 403, comprised in the first surface 310, proximate the stimulation electrode 200, 220, configured to provide, in use, a corresponding electrical return for the stimulation electrode 200, 220;
wherein:
the return electrode 400, 401, 402, 403 is elongated along the longitudinal axis 600; and
the return electrode 400, 401, 402, 403 has a longitudinal extent substantially greater than the transverse extent of the return electrode 400, 401, 402, 403.

F.2 The implantable stimulation device according to F1, wherein:
the return electrode 400, 401, 402, 403 has a longitudinal extent greater than or approximately equal to the longitudinal extent of the stimulation electrode 200, 220.

F.3 The implantable stimulation device according to F1 or F2, wherein:
the return electrode 400, 401, 402, 403 has a transverse extent greater than or approximately equal to the transverse extent of the stimulation electrode 200, 220.

F.4 The implantable stimulation device according to F1, F2 or F3, wherein:
an active tissue contact-area of the return electrode 400, 401, 402, 403 is equal to or more than the active tissue contact-area of the one or more stimulation electrodes 200, 220 configured to be active during use.

F.5 The implantable stimulation device according to F1, F2, F3 or F4, wherein:
the number of non-contiguous return electrode regions a,b,c,d is less than or equal to the number of non-contiguous stimulation electrodes 200, 220.

FOR EXAMPLE

An implantable stimulation device 100, 101, 102, 103 comprising:
an elongated substrate 300, disposed along a longitudinal axis 600, the substrate having a first 310 and second 320 surface disposed along substantially parallel transverse planes 600, 700, the substrate 300 further comprising:
a stimulation electrode 200, 220, comprised in the second surface 320 and configured to transmit energy, in use, to human or animal tissue, the stimulation electrode 200, 220 having a longitudinal extent along the longitudinal axis 600 and a transverse extent along a first transverse axis 700, the transverse axis 700 being substantially perpendicular to the longitudinal axis 600 and substantially parallel to the second surface 320; and
a return electrode 401, 402, 403, comprised in the first surface 310 or second surface 320, proximate the stimulation electrode 200, 220, configured to provide, in use, a corresponding electrical return for the stimulation electrode 200, 220;
wherein:
the return electrode 401, 402, 403 comprises two transversely-separated electrode regions a, b, c, d elongated along the longitudinal axis 600, electrically connected to each other, the two electrode regions a, b, c, d being disposed on opposing transversal 700 sides of the stimulation electrode 200, 220;
the two electrode regions a, b, c, d have a longitudinal extent greater than or approximately equal to the longitudinal extent of the stimulation electrode 200, 220; and
each electrode region a, b, c, d is transversely separated from the stimulation electrode 200, 220 by an electrical insulator.

REFERENCE NUMBERS USED IN DRAWINGS 100 a first type of implantable end of a tissue stimulation system
101 a second type of implantable end of a tissue stimulation system
102 a third type of implantable end of a tissue stimulation system
103 a fourth type of implantable end of a tissue stimulation system
150 a stimulation energy source
200 one or more stimulation electrodes
220 an elongated stimulation electrode
250 one or more electrical interconnections
300 an elongated substrate
310 a first substantially planar transverse surface
320 a second substantially planar transverse surface
330 a first transverse extent
340 a second transverse extent
350 substrate protrusion for a return electrode
400 a first type of one or more proximal return electrodes
401 a second type of one or more proximal return electrodes
401ab a first and second region of a second type of proximal return electrode
402 a third type of one or more proximal return electrodes
402ab a first and second region of a third type of proximal return electrode
403 a fourth type of one or more proximal return electrodes
403ab a first and second region of a fourth type of proximal return electrode
450 one or more distal return electrodes
550 a pulse energy controller
570 electric potential
600 a longitudinal axis
700 a first transverse axis
750 a second transverse axis
810 location for left supraorbital nerve or cortical stimulation
820 location for right supraorbital stimulation
830 location for left occipital nerve stimulation
840 location for right occipital nerve stimulation
850 location for deep brain stimulation
860 location for vagus nerve, carotid artery, carotid sinus, phrenic nerve or hypoglossal stimulation
865 location for cerebral spinal cord stimulation
870 location for peripheral nerve stimulation
875 location for spinal cord stimulation
880 location for gastric stimulation
885 location for sacral & pudendal nerve stimulation
890 location for sacral neuromodulation
895 location for fibular nerve stimulation
910 left supraorbital nerve
920 right supraorbital nerve
930 left greater occipital nerve
940 right greater occipital nerve
1200 proximal resistive tissue
1250 distal resistive tissue
1400 proximal variable resistor
1425 rheostat
1450 distal variable resistor
1550 energy source

The invention claimed is:
1. A tissue stimulation system comprising:
an implantable end and a stimulation energy source;
the implantable end comprising:
a substrate supporting one or more stimulation electrodes and one or more proximal return electrodes; and the stimulation energy source comprising:
one or more distal return electrodes disposed distantly from the one or more stimulation electrodes; and
a pulse generator supported by the substrate;
the tissue stimulation system further comprising one or more interconnections between the implantable end and the stimulation energy source, to connect the output of the pulse generator to the one or more stimulation electrodes such that electrical energy is transferred, as one or more stimulation pulses, from the pulse generator to the one or more stimulation electrodes;
wherein:
the one or more proximal return electrodes are a first part of the electrical return for the one or more stimulation electrodes; and
the one or more distal return electrodes are a second part of the electrical return for the one or more stimulation electrodes.

2. The tissue stimulation system according to claim 1, wherein the one or more distal return electrodes are disposed more than 18 mm from the one or more stimulation electrodes.

3. The tissue stimulation system according to claim 1, wherein the one or more proximal return electrodes are disposed within less than 8 mm from the one or more stimulation electrodes.

4. The tissue stimulation system according to claim 1, wherein:
the one or more proximal return electrodes are elongated along a longitudinal axis of the substrate.

5. The tissue stimulation system according to claim 1, wherein:
the one or more stimulation electrodes have a first extent along a longitudinal axis of the substrate, and the one or more proximal return electrodes have a second extent along the longitudinal axis of the substrate, the second extent being substantially the same or greater than the first extent.

6. The tissue stimulation system device according to claim 1, wherein:
the one or more stimulation electrodes are elongated along a longitudinal axis of the substrate.

7. The tissue stimulation system according to claim 1, wherein:
the one or more proximal return electrode comprises two proximal return electrode regions, electrically connected to each other, the two proximal return electrode regions being disposed on opposing sides of the one or more stimulation electrode.

8. The tissue stimulation system according to claim 7, wherein:
the two proximal return electrode regions are two non-contiguous electrode regions, electrically connected to each other; and each return electrode region is separated at least partially along the first transverse axis from the one or more stimulation electrodes by an electrical insulator.

9. The tissue stimulation system according to claim 7, wherein:
the two proximal return electrode regions are comprised in a substantially contiguous proximal return electrode.

10. The tissue stimulation system according to claim 7, wherein one or more of the two proximal return electrode regions extend along a first transverse axis of the substrate between an edge of one or more of the stimulation electrodes and an edge of the substrate.

11. The tissue stimulation system according to claim 1, wherein:
a further proximal return electrode is disposed on the substrate.

12. The tissue stimulation system according to claim 1, wherein each of the one or more stimulation electrodes has a corresponding proximal return electrode of the one or more proximal return electrodes.

13. The tissue stimulation system according to claim 1, wherein the substrate comprises a material selected from the group consisting of: a Liquid Crystal Polymer LCP, a Polyimide, parylene, a biocompatible polymer, a biocompatible elastomer, and combinations thereof.

14. The tissue stimulation system according to claim 1, wherein the one or more proximal return electrodes and the one or more distal return electrodes have a combined tissue-contact area no less than a tissue contact-area of the one or more stimulation electrodes.

15. A method of tissue stimulation, comprising:
using the tissue stimulation system according to claim 1 to stimulate a body part selected from the group consisting of: one or more nerves, one or more muscles, one or more organs, spinal cord tissue, and combinations thereof.

16. A method of treatment, comprising:
using the tissue stimulation system according to claim 1 to treat a condition selected from the group consisting of: headaches, primary headaches, incontinence, occipital neuralgia, sleep apnea, hypertension, gastroesophageal reflux disease, an inflammatory disease, limb pain, leg pain, back pain, lower back pain, phantom pain, chronic pain, epilepsy, an overactive bladder, poststroke pain, obesity, and combinations thereof.

17. The tissue stimulation system according to claim 1, wherein at least one of:
the one or more interconnections are embedded in the substrate, and
the substrate comprises a low conductance or insulating material such that the substrate prevents the one or more interconnections from physically contacting one or more bodily tissues when the one or more stimulation electrodes are implanted to physically contact the one or more bodily tissues.

18. The tissue stimulation system according to claim 1, further comprising a ratio controller for modifying an electrical ratio of the one or more proximal return electrodes to the one or more distal return electrodes.

19. The tissue stimulation system according to claim 18, wherein the pulse generator comprises the ratio controller.

20. The tissue stimulation system according to claim 18, wherein the ratio controller comprises:
a first variable resistor connected between the one or more proximal return electrodes and the electrical return for the one or more stimulation electrodes, and
a second variable resistor connected between the one or more distal return electrodes and the electrical return for the one or more stimulation electrodes.

21. The tissue stimulation system according to claim 1, wherein the pulse generator is directly connected to the substrate.

22. A tissue stimulation system, comprising:
a substrate having a first end and a second end, the first end being disposed longitudinally opposite to the second end, the substrate comprising:
a first surface extending continuously from the first end to the second end, and a second surface extending continuously from the first end to the second end, the second surface being disposed opposite to the first surface;

one or more stimulation electrodes physically attached to the first surface on the first end;

one or more proximal return electrodes physically attached to the first end;

one or more distal return electrodes disposed on the second end such that the one or more distal return electrodes are physically farther from the one or more stimulation electrodes than the one or more proximal return electrodes;

a pulse generator supported by the substrate; and one or more interconnections embedded in the substrate, to electrically connect an output of the pulse generator to the one or more stimulation electrodes.

23. The tissue stimulation system of claim 22, wherein the substrate comprises a low conductance or insulating material such that the substrate prevents the one or more interconnections from physically contacting one or more bodily tissues when the one or more stimulation electrodes are implanted to physically contact the one or more bodily tissues.

24. The tissue stimulation system of claim 22, wherein the one or more interconnections provide an electrical return for the one or more stimulation electrodes using the one or more proximal return electrodes and the one or more distal return electrodes.

* * * * *